United States Patent [19]
Gardon

[11] Patent Number: 5,997,969
[45] Date of Patent: Dec. 7, 1999

[54] NON-ALLERGENIC MEDICAL AND HEALTH CARE DEVICES MADE FROM CROSSLINKED SYNTHETIC ELASTOMERS

[76] Inventor: John L. Gardon, 6080 Snowshoe Cir., Bloomfield Hills, Mich. 48301

[21] Appl. No.: 09/141,205

[22] Filed: Aug. 27, 1998

[51] Int. Cl.$^6$ ................................................... A41D 19/00
[52] U.S. Cl. ................................. 428/35.7; 2/167; 2/168
[58] Field of Search .............................. 428/35.7; 2/167, 2/168

[56] References Cited

U.S. PATENT DOCUMENTS

| | | |
|---|---|---|
| 3,813,695 | 6/1974 | Podell, Jr. et al. .......................... 2/168 |
| 3,872,515 | 3/1975 | King et al. . |
| 4,463,156 | 7/1984 | McGary, Jr. et al. ...................... 528/65 |
| 4,576,156 | 3/1986 | Dick et al. . |
| 4,684,490 | 8/1987 | Taller et al. . |
| 5,014,361 | 5/1991 | Gray . |
| 5,088,125 | 2/1992 | Ansell et al. . |
| 5,195,537 | 3/1993 | Tillotson et al. . |
| 5,248,157 | 9/1993 | Miller et al. . |
| 5,272,771 | 12/1993 | Ansell et al. . |
| 5,458,936 | 10/1995 | Miller et al. . |
| 5,500,469 | 3/1996 | Johnsen et al. . |
| 5,534,350 | 7/1996 | Liu et al. . |
| 5,545,451 | 8/1996 | Haung et al. . |
| 5,612,083 | 3/1997 | Haung et al. . |
| 5,620,773 | 4/1997 | Nash et al. . |
| 5,636,382 | 6/1997 | Chopko et al. . |

FOREIGN PATENT DOCUMENTS 92-200919 2/1992 European Pat. Off. .

*Primary Examiner*—Charles Nold
*Attorney, Agent, or Firm*—Dykema Gossett PLLC

[57] ABSTRACT

This invention provides means to replace vulcanized natural rubber with non-allergenic synthetic rubbers in the manufacture of health care devices such as protective gloves, condoms, tourniquets and dental dams. The synthetic rubbers are latexes and aqueous polyurethane dispersions having very low glass transition temperatures and crosslinked by means other than sulfur vulcanization of double bonds.

19 Claims, No Drawings

NON-ALLERGENIC MEDICAL AND HEALTH CARE DEVICES MADE FROM CROSSLINKED SYNTHETIC ELASTOMERS

FIELD OF THE INVENTION

The invention relates generally to medical devices formed of synthetic polymeric materials. More specifically, this invention provides a family of medical devices based on novel synthetic elastomers having elastic and tactile properties equal to or better than those based on natural rubber. These devices include protective gloves, condoms, tourniquets, dental dams and the like. Unlike medical devices based on natural rubber, those based on the novel synthetic elastomers of the present invention are non-allergenic.

BACKGROUND OF THE INVENTION

In the current state of the art medical devices based on thin film elastomers are manufactured predominantly from vulcanized natural rubber. Usually the film thickness is 3 to 15 mils. Vulcanized natural rubber (VNR) offers particular advantages for protective gloves used by surgeons, dentists and veterinarians who need tactile feel and resilient glove material for their delicate operations. An other class of medical gloves are referred to as "examination gloves." These provide to health care givers and patients protection against viruses and bacterial attack in activities not requiring high level of delicate manual dexterity. Specifically, tactile feel is not an important requirement for examination gloves. In the current state of the art, examination gloves are made of from either VNR or from synthetic rubbers such as nitrile rubber, poly(chloroprene) or plastisized poly(vinyl chloride). In the medical device trade poly(chloroprene) is referred to simply as chloroprene or Neoprene™. Plasticized poly(vinylchloride) is often called "vinyl" in the medical device trade. This terminology will be used herein.

Vulcanized natural rubber is also widely used for tourniquets and dental dams in the health care field. Excellent tactile response and resilience are properties which are crucial for the use of VNR for making condoms.

In summary, synthetic elastomers are useful for examination gloves but, at the present state of the art, do not meet the needs for more delicate medical devices; that is, surgical (including dental and veterinary) gloves, and condoms (for the latter end-uses VNR is almost exclusively used).

The single major shortcoming of VNR is that it causes allergies in a significant fraction of the human population. Reliable statistics are not available but the literature indicates that about 1% of the population is susceptible to the so called "latex allergy."

The major cause of latex allergy is the presence of protein in natural rubber latex. Natural rubber is tapped from rubber trees or rubber plants in form of an aqueous dispersion (latex) and the protein is nature's means to provide colloidal stability to these dispersions. The protein content in VNR can be reduced by using special sources of low protein rubbers or by aqueous extraction. Articles made with low-protein VNR are referred to as hypo-allergenic. The indication is that even minute levels of protein can cause allergies in some people. An objective of the present invention is to provide elastic medical devices which are completely non-allergenic.

Proteins are not the only allergenic ingredients in VNR based devices. For achieving the desired elastic and barrier properties, the rubber must be vulcanized. In this process sulfur-based links are introduced between individual molecules during the curing of the articles. In vulcanization certain accelerators must be used, such as amines, carbothiazoles, sulfonimides, thiocarbamates and thiourams. Some or all of these accelerators are also causes of allergies. In fact, nitrile rubber crosslinked by methods of vulcanizing natural rubber is allergenic though it is completely protein free. The major objective of the present invention is to provide articles made from completely non-allergenic synthetic rubbers crosslinked by completely non-allergenic means.

Most medical devices in the field of this invention are currently made from VNR, chloroprene, nitrile rubber and vinyl. Vinyl is a category by itself. Pure poly(vinylchloride) is not rubbery and is rendered rubbery by plasticizers. Also, the vinyl articles in the field of this invention are most often prepared from water-free plastisols and cannot be made resilient by crosslinking.

Natural rubber, polychloroprene and nitrile rubber are supplied as aqueous polymer dispersions, specifically as latexes. These three latex polymers have a crucially important structural feature in common: they are based on diene monomer building blocks with double carbon—carbon unsaturation. The structure of the dienes is shown below:

$$CH_2=CHR-CH=CH_2$$

Here R is H for butadiene, $CH_3$ for isoprene and Cl for chloroprene.

When the dienes are polymerized, each converted monomer retains a single unsaturation as illustrated in the polymer structure below:

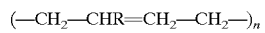

$$(-CH_2-CHR=CH_2-CH_2-)_n$$

Natural rubber is pure polyisoprene. Nitrile rubber is a copolymer of acrylonitrile and butadiene in the 20/80 to 40/60 ratio and is often modified with carboxylic monomers. Polychloroprene is most often made substantially without comonomers.

The unsaturation in the polymer chain is the crosslink acceptor in the vulcanization of natural rubber or nitrite rubber. As stated earlier, the accelerators used in vulcanization with sulfur are allergenic.

The major disadvantage of unsaturation in the diene rubbers is poor stability against heat, radiation and oxidation. Sterilization and packaging after sterilization is rather expensive. The devices made from saturated polymers according to the present invention have the advantage of superior heat, radiation, oxidation and storage stability. A special embodiment of the present invention provides novel inexpensive means for sterilization of medical devices.

U.S. Pat. Nos. 3,872,515 (Mar. 25, 1975, K. G. King et al.) and 5,620,773 (Apr. 15, 1997, B. Nash et al.) teach the use of non-allergenic aqueous silicone based dispersion polymers for making elastic medical devices. The exorbitantly high cost of silicone elastomers precludes their use in the present field of invention.

U.S. Pat. No. 5,500,469 (Mar. 19, 1996, K. E. Johnsen et al.) teaches the use of an aqueous dispersion of copolymer containing hard non-rubbery monomer blocks and diene monomer based rubbery blocks in the same molecule. This polymer is not crosslinked on curing. Instead, the hard blocks provide some resilience to the shaped articles.

Several U.S. patents propose the use of polyurethanes for elastic medical devices.

Two patents teach the application of thermoplastic urethane rubber elastomers to condom shaped mandrels with subsequent curing. In U.S. Pat. No. 4,576,156 (Mar. 18, 1986, M. F. Dyck et al.) the proposed curing temperature is 400 to 450° F. In U.S. Pat. No. 4,684,490 (Aug. 8, 1987, R. A. Taller et al.) the curing temperature is lower, 265 to 350° F. It is also known that the urethane bonds break and rearrange at temperatures above 280° F. leading to crosslinking. These patents do not teach that the urethane rubber be applied from an aqueous dispersion and do not anticipate crosslink formation during heat curing.

U.S. Pat. Nos. 3,813,695 (Jun. 4, 1974, D. L. Dodell et al.), 5,272,771 (Feb. 18, 1992, C. W. Ansell et al.) and 5,534,350 (Dec. 28, 1994, D. Liu et al.) teach lining of VNR gloves with uncrosslinked polyurethanes can be useful either for rendering them hypoallergenic or for improving their donning properties and eliminating the need to use powder to lubricate them internally. U.S. Pat. No. 5,545,451 (Aug. 13, 1996, W. N. Huang et al.) teaches the use of both acrylic latexes and polyurethane dispersions in multilayer VNR based powderless gloves.

SUMMARY OF INVENTION

In one aspect, the present invention provides means to replace vulcanized natural rubber with non-allergenic synthetic rubbers in the health care devices such as protective gloves, condoms, tourniquets, dental dams and the like. The synthetic rubbers are latexes and aqueous polyurethane dispersions having very low glass transition temperatures and crosslinked by means other than sulfur vulcanization of double bonds.

Thus, the preferred embodiment of the present invention involves the use of synthetic polymers substantially free of carbon—carbon unsaturation and having better stability than diene based rubbers for medical devices which contact living tissue. However, diene monomers can be used in practicing the present invention as long as the resulting rubbers are crosslinked not by sulfur vulcanization but by means which are the essential features of the present invention.

According to the present invention non-allergenic elastomers for medical devices are based on synthetic latexes made by free radical polymerization or on aqueous polyurethane dispersions. In accordance with the present invention, these rubbers are chemically crosslinked while the devices are cured into their final shape.

The crosslinked polyurethane or synthetic latex rubbers of the present invention have the strength to be the sole ingredient for making gloves. The properties of these novel rubbers can be optionally adjusted for the manufacture of powderless gloves. In one aspect, the present invention provides novel means for adjusting complete resilience or some resilience with specifiable stress relaxation. This can now be accomplished by blending crosslinkable and non-crosslinkable rubber dispersions of various $T_g$ values in the dipping and casting bath.

Thus, it will be appreciated that the present invention provides medical and health care devices such as gloves, condoms, tourniquets and dental dams having a non-allergenic surface. The non-allergenic surface is adapted to contact living tissue of humans or animals and comprises a non-allergenic synthetic polymer formed from an aqueous dispersion of polymers. The polymers of the aqueous dispersion are selected from the group consisting of latexes and polyurethanes, and blends and interpolymers thereof. As will be understood, the solid polymers of the aqueous dispersions have glass transition temperatures less than about 0° C. according to this invention. Also, the polymers of the aqueous dispersions have number average molecular weights of higher than about 100,000. Finally, the polymers of the aqueous dispersions have the capacity to crosslink through the use of crosslinkers which activate crosslink accepting functionalities. According to a preferred embodiment of the present invention the crosslink accepting functionalities are selected from the group consisting of hydroxyl and carboxyl functionalities.

In one aspect the crosslink accepting functionality is a hydroxyl group and the crosslinkers are selected from the group consisting of amino resins, diacetals of aldehydes, multifunctional isocyanates and multifunctional blocked isocyanates. In another aspect, the crosslink accepting group is a carboxyl and the crosslinkers are selected from the group of multifunctional carbodiimides, azridines, epoxies, hydroxyethylamides or amine complexes of zinc or zirconium.

In one aspect the aqueous dispersions are self-crosslinking latexes synthesized by copolymerizing into them both Type A and Type B functional monomers which are mutually reactive on heat curing of films. The functionality of Type A is selected from the group consisting of hydroxymethyl amide, $C_1$ to $C_4$ alkoxymethyl amide, isocyanate or blocked isocyanate and the Type B functionality is selected from the group consisting of amide and $C_2$ to $C_4$ hydroxyalkyl.

In one aspect the aqueous dispersions are polyurethane dispersions having the capacity to self-crosslinking at temperatures within the range of about 280 to about 500° F.

In another aspect the aqueous dispersions are latexes synthesized by copolymerizing into them functional monomers selected from the group consisting of acetoxyethyl methacrylate, diacetone acrylamide, epoxy functional monomers and cyclic carbonate functional monomers and the crosslinkers are selected from the group consisting of multifunctional amines and multifunctional carbohydrazides.

In still another aspect the aqueous dispersions comprise blends of polymers, one which does and one which does not crosslink. The ratio of these two polymers is 20/80 to 80/20.

In one aspect the aqueous dispersions contain blends of rubbers with harder rubbers having a glass transition temperature in the range of 0 to T° C. and the softer ones below (T–10)° C. where T is in the range of –10 to –30° C. and where one or the other components comprise at least 30% of the dispersions.

In one aspect the aqueous dispersions are synthesized without using diene monomers.

In one aspect the aqueous dispersions further include pigments and/or fillers.

The present invention also provides a method of sterilizing surgical, veterinary and dental gloves wherein the gloves are opaque to ultraviolet radiation. The gloves are sterilized on the hands of the health care givers by exposure to ultraviolet light.

DETAILED DESCRIPTION OF THE INVENTION

The medical devices of the present invention are preferably produced either by dip processing or by casting of films. Suitable molds or mandrels are dipped into an aqueous polymer dispersion. As a mold is withdrawn, it becomes covered by a layer of aqueous polymer. Multiple dipping is optional. In multiple dipping a coagulant may be impinged upon the film. Finally the film is cured either for a few minutes at 250 to 500° F. or much longer at lower curing temperatures such as 120 to 180° F. The details of the forming of medical devices by the dipping process is well known to those skilled in the art. Alternately, films are cast into flat sheets and are treated similarly to products made by dipping.

The dipping bath of the present invention consists of a synthetic latex or a polyurethane dispersion (PUD) or a blend of such materials. Generally, these polymers are more rubbery than their harder counterparts which are useful not as free films but as permanent modifiers of substrates as in paints, coatings, finishes for flexible materials (textile, paper and leather), adhesives and sealants. Both latexes and PUDs are synthetized as colloidal aqueous dispersions of tiny particles having 40 to 500 nm diameter. The molecular weights of these polymers is high, above 40,000, preferably above 100,000 and up to few million Daltons. Preferably, the latex and PUDs have number average molecular weights higher than about 40,000.

The latex or PUD based films require crosslinking for most though not all applications within the present field of invention. The crosslinker is dispersed or dissolved into the dipping bath. This polymer-crosslinker system has limited reactivity at ambient temperature. The potlife of such formulated system is not shorter than three hours if the article is to be cured at low temperature, such as 120 to 180° F., and spans over several months for curing temperatures above 220° F. The coated mold or cast film is finally exposed to an elevated temperature for cure. The final product becomes crosslinked during the curing process.

An overview of latexes, PUDs and crosslinkers is provided by J. L. Gardon (pp. 27–43, "Technology for Waterborne Coatings", J. E. Glass, Editor, ACS Symposium Series 663, 1997). A recent book on synthetic latexes is that of M. S. El-Asser and P. Lovell ("Emulsion Polymerization and Emulsion Polymers", Wiley, New York, 1997). The synthesis and application of PUDs is described by J. W. Rothauser (pp. 121–162, "Advances in Urethane Science and Technology", K. C. Frisch, Editor, Vol. 10, 1987), by D. Dietrich (Progress Org. Coatings, Vol. 9, pp. 281–195, 1981) and by J. C. Padget (J. Coatings Technology, Vol. 66, pp. 89–97, December 1994).

Synthetic Latexes

In the present invention, a synthetic latex is prepared by aqueous reaction of a blend of unsaturated monomers which yields a water insoluble polymer. The reaction mixture contains from about 0.05 to about by weight 1% free radical initiator, such as a persulfate salt, an organic peroxide or hydroperoxide or a suitable azo compound. Optionally a reducing agent such as sodium bisulfite or ascorbic acid is used to increase the activity of the initiator. Another ingredient is from about 0.5 to about 8% of a compound for enhancing colloidal stability of the dispersion and for reducing the particle size during polymerization. Such compound can be a protective colloid, such as poly(vinyl alcohol), or an anionic surfactant such a sodium lauryl sulfate or a nonionic surfactant such as an ethylene oxide adduct to an alkyl phenol. There is a tremendous variety of initiators and colloidal stabilizers. Their choice is not an essential feature of the present invention with the proviso that they be non-allergenic when their remnants are present in dry films. This condition is satisfied by practically all of these types of ingredients which are used in the current industrial practice of paints, coatings, textile and paper finishes, adhesives and sealants.

For most applications the latexes useful for this invention must be resilient elastomers. Resiliency is achieved by crosslinking but without recourse to vulcanizing with sulfur through unsaturation in the chain molecules. For this, the monomer composition must satisfy at least two criteria: the uncrosslinked polymer must have a low glass transition temperature and it must have reactive sites for accepting crosslinks.

The glass transition temperature ($T_g$) is an important characteristic of all polymers. At a temperature above the $T_g$ the chain segments of a polymer are mobile and the bulk polymer Is easily deformed; below the $T_g$ the polymer is glassy, i.e. rigid. Latexes of a great variety of $T_g$ values can be designed based on well established scientific principles. Certain monomers are generally referred to be soft because their homopolymers have $T_g$ values below 15 to 20° C. so that they are rubbery under ambient conditions. Conversely, hard monomers yield glassy homopolymers having high $T_g$ values. The $T_g$ values of polymers are conveniently determined by thermomechanical methods. In modern practice such determination is not needed because the $T_g$ values characteristic for commonly used unsaturated monomers are extensively tabulated and the $T_g$ of a random and noncrystalline copolymer composition can be calculated.

As an illustration, the characteristic $T_g$ values (° C.) of some more important monomers are shown below in parentheses:

| | |
|---|---|
| Dienes: | butadiene (−83), isoprene (−72), chloroprene (−45) |
| Other soft monomers: | ethylene (−80), octyl acrylate (−65), butyl acrylate (−54), ethyl acrylate (−24), vinyl ester of a branched $C_{10}$ acid (−4), vinyl butyl ether (−52), vinyl ethyl ether (−19), vinyledene chloride (−22). |
| Hard monomers: | vinyl acetate (+34), isobutyl methacrylate (+55), vinyl chloride (+80), acrylonitrile (+100), styrene (+100) methyl methacrylate (+105) |

It is evident that a great variety of monomer combinations can lead to rubbery synthetic copolymer latexes. Latexes useful to this inventions are based not only on monomers listed above. Many other monomers are available as well known to those skilled in the art. The non-diene soft monomers yield rubbers which are free of unsaturation and more stable than the diene based rubbers. To be useful for this invention the latexes must have $T_g$ values below 0° C. The preferred embodiment of this invention requires $T_g$ values below −15° C.

Uncrosslinked rubbery polymers lack resilience; they do not return to their original shape once deformed. The present invention requires that the latex polymers contain crosslink accepting sites. As will be shown later, carboxyl (—COOH) and hydroxyl (—OH) groups allow the use a variety of external crosslinkers though other crosslink accepting groups are also useful for the present invention. Carboxyls are conveniently introduced by copolymerizing into the latex acrylic, methacrylic, itaconic or other unsaturated acids. Useful hydroxyl functional monomers include hydroxy alkyl (ethyl, propyl or butyl) acrylate, methacrylate, acrylamide or methacrylamide. In this context the desired carboxyl or hydroxyl equivalent weight should be 500 to 10000. This requirement is satisfied if the latex contains 0.02 to 4% by weight of these functional monomers.

Crosslinking through the aforementioned crosslink accepting sites is accomplished after the latex is dried into the final shape of the device to be made, and is cured.

The monomers of the preferred embodiment of this invention are vinyl monomers. Unlike diene monomers, vinyl monomers do not contain conjugated unsaturation. Conjugated unsaturation is characteristic to dienes where two double bonds originate on two adjacent carbon atoms, as shown above. Most vinyl monomers have a single unsaturation on their molecules. For example, the structure of n-butyl acrylate is shown below.

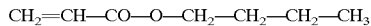

However, there are multifunctional vinyl monomers useful for this invention which have multiple unsaturation on the molecules but the double bonds are separated to greater extent than in dienes. An example is butylene glycol diacrylate:

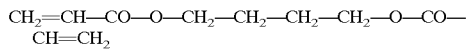

There are numerous other divinyl or trivinyl monomers available, such as trimethylolpropane triacrylate and divinyl benzene. Such monomers can be copolymerized in small quantities, 0.1 to 3%, into predominantly monovinyl monomer based latexes and cause crosslinking during polymerization. Latexes crosslinked in this manner are not useful as the sole constituent for making the devices of this invention. Such precrosslinked latexes can be blended with latexes which become crosslinked only after high temperature curing. Also, precrosslinked latexes can be used to create unique particle morphology. First a precrosslinked latex is synthesized and provides the core of the final latex. Onto this core a polymer shell is layered which is not precrosslinked but contains crosslinkable groups reactive under heat cure. Devices of the present invention made from such two component latexes have unique physical properties.

Devices based on synthetic latexes containing diene monomers are useful for the present invention as long as their inferior stability to heat, radiation and oxydation is acceptable. Devices made of diene containing latexes crosslinked according the embodiments of the present invention have advantages over those crosslinked by sulfur vulcanization in that the allergy causing crosslinking chemicals are avoided. A preferred embodiment of the present invention involves the use of nitrile rubber containing carboxyl or hydroxyl functional vinyl monomers and crosslinked by methods of the present invention which apply to these functional groups.

Polyurethane Dispersions

In another embodiment, polyurethane dispersions are used to form the non-allergenic devices. Polyurethane dispersions are similar to latexes in particle size and molecular weight. Films cast from PUDs tend to be more resilient and more solvent resistant than latex films at about equal $T_g$ and about equal degree of crosslinking.

The synthesis of a typical carboxyl functional PUD starts with the synthesis of a prepolymer in a nonaqueous medium. The starting material is a linear diol having one hydroxyl group at each end of the molecule. Such diol has a number average molecular weight of from about 500 to 10000 and is preferably based either on a polyester or on a polyether. Typically two moles of such a diol are reacted with 1 mole of dimethylol propionic acid and four moles of a diisocyanate. The resultant prepolymer contains, per number average molecule, two chain end isocyanate groups, one carboxyl group and four mid-chain urethane groups. This prepolymer is diluted with a few % of a water miscible organic solvent to reduce its viscosity and is neutralized with a tertiary amine. Subsequently it is mechanically emulsified into water. Immediately a diprimary amine (for example hexane diamine) is added at a 1/1 strochiometric ratio of amine to isocyanate. The newly formed urea links extend the molecular weight to well above 40,000 Daltons.

The PUDs useful for the present invention, similarly to latexes, must be rubbery with $T_g$ values below 0° C. and preferably below −15° C. The dominating factor for $T_g$ of a PUD is the diol of the prepolymer. A few $T_g$ values (° C.) of polyesters and polyethers are shown below:

| | |
|---|---|
| poly(ethylene adipate) (−50) | poly(ethylene oxide) (−67) |
| poly(decamethylene adipate) (−56) | poly(propylene oxide) (−75) |
| poly(ethylene terephthalate) (+60) | poly(butylene oxide) (−70) |

The urethane and urea links in the PUD molecules somewhat increase the $T_g$ relative to that of the diols but this is acceptable. Isocyanates useful for PUD synthesis include methyl diphenyl isocyanate (MDI), hydrogenated MDI, toluene diisocyante, isophoron diisocyanate, trimethylhexamethylene diisocyanate, tetramethyl-xylelene diisocyanate, xylelene diisocyante, and allophenate or uretdione dimer of hexamethylene diisocyanate.

Uncrosslinked, the PUDs tend to be more resilient than latexes. Nevertheless, crosslinking most often enhances their utility. Carboxyl is the most convenient crosslink acceptor group on a PUD. The carboxyl equivalent weight is easily brought into the range useful for this invention by changing the ratio of the reactants. Hydroxyl functional PUDs can also be prepared by using hydroxyl functional diamines such as 1,3-diamino -2-hydroxy propane for chain extension of the prepolymers.

Pendant acrylic double bonds can be introduced into a PUD by several means. For example the use of a small amount of a triisocyanate in addition to diisocyanate in the preparation of the prepolymer provides sites for reaction with hydroxyethyl acrylate. Such acrylic modified PUDs are crosslinkable by electromagnetic radiation. They are also useful for grafting sites to acrylic polymers.

The PUDs useful for this invention are not confined to those based on reactants and synthesis methods mentioned above. There are many synthesis methods and compositions for synthesizing colloidal poly(urethane-urea) polymers which are rubbery and optionally crosslinkable.

The preferred embodiment of this invention involves PUDs based on linear molecules and colloidally stabilized in water by carboxyl groups. Linearity is achieved by the application of difunctional diols, diisocyanates and diamines in the synthesis as in the example shown above. However for modification of rheology and for introduction of crosslink accepting groups branched PUDs are needed. Branching is achieved during synthesis by the application of branched prepolymers and/or of triisocyantes replacing part of the diisocyanates and/or of triamines replacing diamines. Colloidal stabilization by sulfate or sulfonate or polyethylene oxide groups replacing carboxyls is also well known to those skilled in the art.

Blends of rubbery latexes and PUDs are also useful for the present invention. Another class of multicomponent aqueous dispersion polymers have interpenetrating network structures. These are prepared either by simultaneous synthesis of PUDs and latexes or by the synthesis of latexes in the presence of preformed PUDs.

Crosslinking through the Hydroxyl Group

For crosslinking through the hydroxyl group the so-called amino resins are particularly useful. The simplest example of this family of crosslinking agents is dihydroxymethyl urea which is the reaction product of two moles of formaldehyde and one mole of urea. Its structure and the crosslinking reaction with pendant hydroxyl groups of a polymer (P—OH) are shown below:

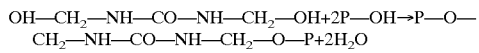
OH—CH$_2$—NH—CO—NH—CH$_2$—OH+2P—OH→P—O—CH$_2$—NH—CO—NH—CH$_2$—O—P+2H$_2$O This reaction is acid catalyzed and heat induced. The crosslinker and the catalyst are added to the polymer dispersion which is neutralized with a volatile amine. The catalyst is an amine salt of a strong acid, for example paratoluene sulfonic acid. After film deposition and during cure at 230 to 260° F. the amine volatilizes and the resulting deblocked free acid causes the crosslinking reaction to proceed. The amino resin is applied in a 1.2 to 5 fold stochiometric access over the hydroxyl group and part of it self condenses.

Numerous amino resins are suited for the present invention. These include hydroxymethylated melamine, glycouril, benzoguanamine, cyclic urea and urea compounds. Depending on the structure they can be 2 to 6 functional. For some of these amino resins the hydroxymethyl groups are etherified either with methanol or with butanol. Solutia Inc. (Springfield, Mass.) and Cytec Industries (West Paterson, N.J.) are two major suppliers of preferred amino resins.

Certain monomers provide self-crosslinking latexes. These are hydroxymethyl acrylamide or methacrylamide and their alkoxylated counterparts. For alkoxylation $C_1$ to $C_4$ alcohols are useful. As an illustration, the structure of hydroxymethyl acrylamide (the one-to-one adduct of formaldehyde and acrylamide) is shown below:

OH—CH$_2$—NH—CO—CH=CH$_2$

Such monomer is readily copolymerized into latexes together with hydroxyalkyl acrylates. No crosslinking takes place during synthesis. On film formation and curing the film becomes crosslinked by the reaction mechanism characteristic to amino resins. Such reaction is close to stochiometric and is particularly useful for precise adjustment level of crosslinking for optimal film properties.

Diacetals of suitable aldehydes also crosslink through hydroxyl groups under cure conditions similar to those applied to amino resins. The dimethyl acetal of glyoxal is combined with the nitrogenous compounds which are otherwise used as precursors for the formaldehyde based amino resins. As an illustration the structure of the monomer suited for selfcrosslinking latexes is shown below:

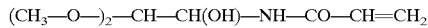
(CH$_3$—O—)$_2$—CH—CH(OH)—NH—CO—CH=CH$_2$

Such diacetals are supplied by the Clairiant Corporation (Charlotte N.C.). Other crosslinkers of this type are based on the dimethyl or diethyl acetal of aminobutyraldehyde (see for example K. Kjellgvist et al, Proceedings of the XIXth International Conference on Organic Coatings, Athens, 1993, p. 281).

It should be noted that amino resin and diacetal crosslinkers react not only with hydroxyl groups; amide and carbamate groups are also useful crosslink acceptors.

Polyisocyanates are useful crosslinkers for hydroxyl functional aqueous polymers but the potlife of the formulated system is short. The preferred embodiment of this invention involves the use of blocked isocyanates such as the reaction product of three moles of a blocking agent (e.g. methyl ethyl ketoxime or epsilon caprolactam or $C_1$ to $C_4$ alcohols) with one mole of a triisocyanate (e.g. the biuret or the isocyanurate trimer of hexane diisocyanete). On heat curing, above 280° F. and most preferably above 350° F., the blocking agent volatilizes and urethane crosslinks are formed between the polymer chains. In the schematic formula below, B is the blocking agent, R is a trifunctional component of the triisocyanate and P is the polymer:

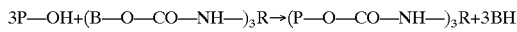
3P—OH+(B—O—CO—NH—)$_3$R→(P—O—CO—NH—)$_3$R+3BH

The present state of the art of blocked isocyanates is described in the book of Z. Wicks et al. ("Organic Coatings, Science and Technology," Wiley, New York, 1994).

In the case of PUD based films the chemistry becomes complicated because upon heating some of the urethane bonds dissociate and become rearranged resulting in crosslinked films, even without the use of external crosslinkers. This rearrangement leads to formation of crosslinks and can be termed as an internal deblocking, i.e. a special case of crosslinking with blocked isocyanates. This rearrangement of bonds in the PUD films is also an example of self-crosslinking illustrated above for latexes.

Crosslinking through the Carboxyl Group

An about trifunctional aziridine compound and an about tetrafunctionl carbodiimide compound are available from Zenaca Resins (Wilmington Mass.) and Union Carbide Corporation (Danbury Conn.), respectively. Latexes or PUDs formulated with these crosslinkers have about three days potlife. The crosslinking reaction proceeds very efficiently under mild cure conditions, in 30 minutes at 120° F. or in shorter times at higher temperatures. The chemistry of the polyaziridine crosslinker is shown below. Here R the about three functional backbone of the crosslinker and P is the polymer.

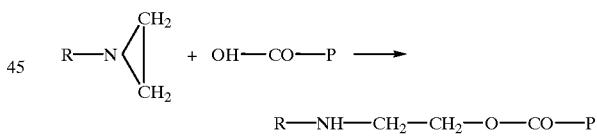

In the formula below R stands for the approximately tetrafunctional backbone of the carbodiimide crosslinker, A is an alkyl group and P is the polymer.

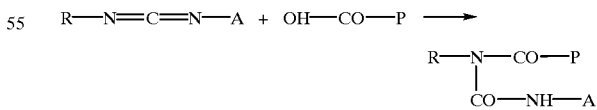

A variety of aliphatic epoxy compounds react with carboxyls above 150° F. preferably catalyzed with a tertiary amine. One of the many suitable reactants is hydrogenated Bisphenol A diglycdyl ether as shown by J. D. Eslinger (J. Coatings Techn., Vol. 67, pp. 45–50, November 1995). In the reaction scheme below R is di- or trifunctional backbone of the epoxyl crosslinker and P is the polymer.

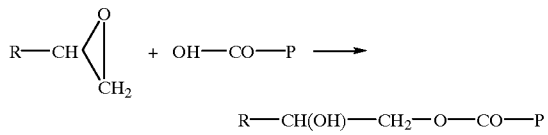

R—CH(OH)—CH$_2$—O—CO—P

Carboxylic polymers react well at elevated temperatures with di- to tetrafunctional hydroxyethylated diamides available from the Rohm and Haas Co. (Philadelphia, Pa.).

Ammonalkaline carboxylic latexes or PUDs blended with an aqueous solution of the amine complex of zinc or zirconium are stable. On drying the ammonia evaporates and zinc or zirconium cations are generated causing the formation of ionic crosslinks.

Some Crosslinking Methods Specific to Latexes

Two monomers contain carbonyl (ketone) groups which chemically activate the adjacent methylene (CH$_2$) groups. Acetoxyethyl methacrylate is supplied by Eastman Chemicals Company (Kingsport, Tenn.) and diacetone acrylamide is supplied by Kyowa Hakko Kogyo Co. Ltd. (Japan). The structures are shown below:

CH$_2$=C(CH$_3$)—CO—O—CH$_2$—CH$_2$—O—CO—CH$_2$—CO—CH$_3$

CH$_2$=CH—CO—NH—C(CH$_3$)$_2$—CH$_2$—CO—CH$_3$

Latexes containing either of these monomers can be crosslinked dicarbohydrazides of diacids or with diamines or triamines at temperatures above 120° F. Under acid catalysis and at temperatures above 220° F. amino resins are effective crosslinkers. Alkaline catalysis promotes reaction at around 180° F. with compounds containing activated double bonds, for example with the acrylic triester of trimethylol propane.

Monomers with a single unsaturation and containing either an isocyanate or an epoxy group are useful for preparing self-crosslinking latexes or latexes which respond to suitable external crosslinkers.

An isocyanate functional monomer is tetramethyl xylylene isocyante available from Cytec Industries (West Paterson, N.J.) with the structure shown below. Here Φ is a benzene ring.

CH$_2$=C(CH$_3$)—Φ—C(CH$_3$)$_2$—N=C=O

The isocyanate group is here highly hindered and does not react with water under the conditions of emulsion polymerization. At elevated temperatures and with a tin catalyst it reacts with hydroxyl groups so that a latex containing it becomes self-crosslinking. This isocyanate is also reactive towards external crosslinkers such as multifunctional amines and carbohydrazides.

A commercially available epoxy functional monomer is glycidyl methacrylate:

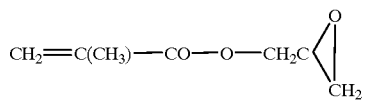

In development are glycidyl acrylate and butadiene monoxide. The structure of the latter is shown below.

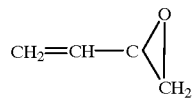

Latexes containing epoxy functional monomers can be crosslinked with multifunctional amines or carbohydrazides. Such latexes also containing carboxyl functional monomers are self-crosslinking at elevated temperatures.

Epoxy functional monomers can be converted to monomers with cyclic carbonate functionality by reacting it with carbon dioxide. Cyclic carbonate functional polymers can be crosslinked with multifunctional amines resulting in urethane containing crosslinks.

Relationship Between Chemical and Physical Properties

This invention provides a large variety of chemical approaches for novel non-allergenic health care devices. Lower Tg values and lower levels of crosslinking make such devices easier to deform. Resiliency improves with higher levels of crosslinking. For good tear strength and puncture resistance there is an optimal crosslink level characteristic to each polymer-crosslinker system. The strength passes through a maximum with increasing level of crosslinking.

The U.S. Pat. No. 5,195,537 (May 10, 1991, N. E. Tillotson et al.) teaches that in some instances it is desirable that the stress of suddenly deformed condoms or surgical gloves should partially relax a few minutes after the deformation. Contrary to this, no stress relaxation is observable in a fully crosslinked rubber. At the other extreme, an uncrosslinked system would not show any resilience. The present invention provides novel means for adjusting complete resilience or some resilience with specifiable stress relaxation. This can now be accomplished by blending crosslinkable and non-crosslinkable rubber dispersions of various T$_g$ values in the dipping and casting bath.

The properties of the films constituting the devices of this invention can be modified by incorporation of hard particulate matters into the rubbers. Such particulate matters can be a hard latex, a pigment, or a filler. Fillers are often used in conjunction with latexes in industry and include clays, silicas, barytes, and calcium carbonate. Up to about 40 volume % of such additives causes increase in the strength and the modulus and reduction in the breaking elongation. Most importantly, pigments change the appearance from transparent to translucent or to opaque. The pigments and fillers are to be dispersed into the dipping and casting baths by means well known to those skilled in the art of making paints and coatings.

A preferred embodiment of the present invention utilizes rubber latexes synthesized without diene monomers. Films prepared from such latexes, and from PUDs, are much more stable to heat, radiation and oxidation than films based on natural rubber. The novel films maintain their original properties under conditions where natural rubber films become embrittled and discolored. This is a significant advantage for efficient sterilization of surgical gloves. A special embodiment of the present invention provides surgical gloves pigmented with titanium dioxide, carbon black or other suitable pigments to render them opaque to ultraviolet radiation. Such gloves can be sterilized on the hands of the health care givers by a brief exposure to ultraviolet radiation in an especially devised box.

The examples below show the synthesis and formulation of three different aqueous rubber dispersions of the present invention. Only the essential ingredients are described. It is understood that a few % of miscellaneous ingredients are also incorporated into the formulated dispersions as needed for the dipping or casting applications. The choice of viscosity modifying thickeners, defoamers, release aids and other additives is well known to those skilled in the art.

The examples specify the cure conditions applicable to films of about 4 to 10 mil dry thickness. On curing these films become crosslinked. The crosslinked films of these examples are substantially insoluble in organic solvents such a tetrahydrofurane, dioxane or various alcohols. When extended by 200% and released, the crosslinked films snap back to their original shapes. While particular embodiments of this invention are shown and described herein, it will be understood, of course, that the invention is not to be limited thereto since many modifications may be made, particularly by those skilled in this art, in light of this disclosure. It is contemplated, therefore, by the appended claims, to cover any such modifications as fall within the true spirit and scope of this invention.

EXAMPLE 1

Devices Based on a Selfcrosslinking Latex

A monomer emulsion is prepared by stirring 68 parts of monomer, 32 parts of water and 4.2 parts (solids) of a nonionic surfactant, the addition product of nonylphenol and 40 ethylene oxide units (Igepal CO 897 of the Rhodia Inc., Cranbury, N.J.). The monomer composition by weight is butoxymethyl acrylamide/hydroxyethyl acrylate/butyl acrylate/acrylic acid=2.6/2/94.4/1.

First 250 gram of a seed polymer is synthesized. The reactor is precharged with 176 g of water, 3 g of an anionic surfactant. (Alipal EP10 of Rhodia Inc., a sulfated adduct of nonylphenol and ethylene oxide) and 17 g of monomer emulsion. This blend is stirred under nitrogen, heated to 70° C. and 54 g of a 2% ammonium persulfate initiator solution is added to it. A fully converted seed polymer is formed in 30 minutes. To prepare the final latex, the temperature is kept at 70° C. and during a 3 hour period 560 g of monomer emulsion and, in a parallel stream, 110 g of a 2% initiator solution is added. The reaction mixture is held at 70° C. for 30 minutes and then 15 g of initiator solution is used as a chaser catalyst to obtain over 99% conversion. Thirty minutes later the solids content is adjusted to 40% and the pH to about 7.5 with 65 g of aqueous ammonia. This recipe provides 1 liter of a latex.

No external crosslinking agent is added to this latex. To provide a crosslinking catalyst, 50 g of a 10% solution of ammonium paratoluene sulfonate is added. The films are dried and cured 30 minutes at 260° F. to become crosslinked.

EXAMPLE 2

Devices Based on a Latex with an External Crosslinker

The embodiments of this example are identical to those of Example 2 with two exceptions. The monomer composition contains no butoxymethyl acrylamide. Also, an external crossslinker is added to the formulated latex. This crosslinker is 55 g of hexamethoxymethyl melamine, available under the trade name Cymel 303 from Cytec Resins.

EXAMPLE 3

Devices Based on a Polyurethane Dispersion Crosslinked with Polycarbodiimide In a resin kettle 22 moles of hexanediol (2552 g) and 20 moles of adipic acid (2920 g) are mixed and rapidly heated under nitrogen to 150° C. The temperature is raised to 200° C. over 20 hours and about 40 moles (720 g) of condensation water is separated in a suitable trap. The reaction is stopped when titration with potassium hydroxide shows a carboxyl content of 0.85 equivalents. At this point the reaction mixture is cooled and 1200 g of terahydrofurane solvent is added to it. At 70° C. 1 mole (176 g) of dimethylol propionic acid and, over 1 hour and cooling, 4 moles (1040 g) of hydrogenated methyl diphenyl diisocyanate are then added resulting in the desired prepolymer. The calculated number average molecular weight of the prepolymer is 5800 Daltons and the solids content of the system is 5800 g. The carboxyl content of the solids is 1.85 equivalents. This organic solution is neutralized with 1.85 moles (189 g) of triethyl amine and stirred into 7700 g of water. Very quickly 1 mole (116 g) of hexane diamine is added under good cooling. The product is 14900 g of an aqueous dispersion having about 40% solids content. The molecular weight of the dispersed solids is well above 100000 and the glass transition temperature is about −45° C.

A crosslinking agent is added to this dispersion. The crosslinking agent is the XL-29E polycarbodiimide of the Union Carbide Corporation. It is applied at 2.5 equivalents (1050 g solids, diluted to 50% in monomethyl ether of propanediol). To become crosslinked, the dried films are cured for 30 minutes at 180° F. or for a shorter time at a higher temperature.

I claim:

1. Medical and health care devices which are non-allergenic, said devices being adapted to contact living tissue of humans or animals, said devices consisting essentially of a resilient, structural body of a non-allergenic synthetic polymer formed from an aqueous dispersion of polymers, said polymers of said aqueous dispersions being selected from the group consisting of polyurethanes and synthetic latexes, said synthetic latexes being formed by free-radical polymerization, and blends and interpolymers thereof, wherein said polymers of said aqueous dispersions have a glass transition temperatures of less than about zero degree Celsius and wherein said polymers of said aqueous dispersions have number average molecular weights higher than about 40,000, and wherein said polymers of said aqueous dispersions have functionalities to crosslink through the use of crosslinkers which are reactive with the crosslink accepting functionalities, where the said crosslink accepting functionalities are selected from the group consisting of hydroxyl, carboxyl, amide, isocyanate, blocked isocyanate, epoxy, carbonyl and carbonyl activated methylene functionalities where the reaction of the said crosslinkers with the said crosslink accepting functionalities is affected by elevated temperature in the range of 120 to 500° F.

2. The medical and health care devices recited in claim 1 wherein the crosslink accepting functionality is a hydroxyl group and the crosslinkers are selected from the group consisting of amino resins, diacetals of aldehydes, multifunctional isocyanates and multifunctional blocked isocyanates.

3. The medical and health care devices recited in claim 1 wherein the crosslink accepting functionality is a carboxyl group and the crosslinkers are selected from the group of multifunctional carbodiimides, aziridines, epoxies, hydroxyethylamides or amine complexes of zinc or zirconium.

4. The medical and health care devices recited in claim 1 wherein the aqueous dispersions are self-crosslinking latexes synthesized by copolymerizing into them both Type A and Type B functional monomers which are mutually reactive on heat curing of films and wherein the functionality of Type A is selected from the group consisting of hydroxymethyl amide, $C_1$ to $C_4$ alkoxymethyl amide, isocyanate or blocked isocyanate and where the Type B functionality is selected from the group consisting of amide and $C_2$ to $C_4$ hydroxyalkyl.

5. The medical and health care devices recited in claim 4 wherein the Type A functionality is epoxy and the Type B functionality is carboxyl.

6. The medical and health care devices recited in claim 1 wherein the aqueous dispersions are polyurethane dispersions having the capacity to self-crosslinking at temperatures within the range of about 280 to about 500° F.

7. The medical and health care devices recited in claim 1 wherein the aqueous dispersions are latexes synthesized by copolymerizing into them functional monomers selected from the group consisting of acetoxyethyl methacrylate, diacetone acrylamide, epoxy functional monomers and cyclic carbonate functional monomers and where the crosslinkers are selected from the group consisting of multifunctional amines and multifunctional carbohydrazides.

8. The medical and health care devices recited in claim 1 wherein the aqueous dispersions comprise blends of polymers, one which does and one which does not crosslink and where the ratio of these two polymers is 20/80 to 80/20.

9. The medical and health care devices recited in claim 1 wherein the aqueous dispersions contain blends of rubbers with harder rubbers having a glass transition temperature in the range of 0 to T° C. and the softer ones below (T–10)° C. where T is in the range of –10 to –30° C. and where one or the other components comprise at least 30% of the dispersions.

10. The medical and health care devices recited in claim 1 wherein the aqueous rubber dispersions are synthesized without using diene monomers.

11. The medical and health care devices recited in claim 2 wherein the aqueous rubber dispersions are synthesized without using diene monomers.

12. The medical and health care devices recited in claim 3 wherein the aqueous rubber dispersions are synthesized without using diene monomers.

13. The medical and health care devices recited in claim 4 wherein the aqueous rubber dispersions are synthesized without using diene monomers.

14. The medical and health care devices recited in claim 5 wherein the aqueous rubber dispersions are synthesized without using diene monomers.

15. The medical and health care devices recited in claim 7 wherein the aqueous rubber dispersions are synthesized without using diene monomers.

16. The medical and health care devices recited in claim 8 wherein the aqueous rubber dispersions are synthesized without using diene monomers.

17. The medical and health care devices recited in claim 1 wherein said devices are selected from the group consisting of protective gloves, condoms, tourniquets, and dental dams.

18. The medical and health care devices recited in claim 1 wherein the aqueous dispersions further include pigments.

19. The medical and health care devices recited in claim 1 wherein the aqueous dispersions further include fillers.

* * * * *